United States Patent [19]
Spickermann

[11] Patent Number: 6,080,321
[45] Date of Patent: *Jun. 27, 2000

[54] DIALYSIS MACHINE FOR THE REMOVAL OF TOXIC SUBSTANCES FROM THE BLOOD WITH AGENTS FOR THE DECALCIFICATION OF A DIALYSIS LIQUID CIRCULATION AS WELL AS PROCESS FOR DETERMINING THE DEGREE OF CALCIFICATION OF A DIALYSIS MACHINE

[75] Inventor: Reiner Spickermann, Wasserlosen-Burghausen, Germany

[73] Assignee: Fresenius Medical Care Deutschland GmbH, Bad Homburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/923,245

[22] Filed: Sep. 4, 1997

[30] Foreign Application Priority Data

Sep. 6, 1996 [DE] Germany .......................... 196 36 255

[51] Int. Cl.[7] .......................... B01D 61/30; B01D 61/32; B01D 65/00; B01D 65/06
[52] U.S. Cl. .............................. 210/739; 210/85; 210/94; 210/95; 210/143; 210/636; 210/646; 210/745
[58] Field of Search ..................................... 210/636, 739, 210/745, 85, 94, 95, 96.2, 103, 143, 646; 422/28

[56] References Cited

U.S. PATENT DOCUMENTS

| | | | |
|---|---|---|---|
| 4,017,190 | 4/1977 | Fischel | 210/96.2 |
| 4,153,544 | 5/1979 | von der Heide | 210/137 |
| 4,695,385 | 9/1987 | Boag | 210/636 |
| 4,897,184 | 1/1990 | Shouldice et al. | 210/96.2 |
| 5,326,476 | 7/1994 | Grogan et al. | 210/646 |
| 5,409,612 | 4/1995 | Malyais et al. | 210/636 |
| 5,487,827 | 1/1996 | Peterson et al. | 210/646 |
| 5,759,489 | 6/1998 | Miura et al. | 422/48 |

FOREIGN PATENT DOCUMENTS

0 648 508 A1  4/1995  European Pat. Off. .

Primary Examiner—John Kim
Attorney, Agent, or Firm—Kenyon & Kenyon

[57] ABSTRACT

A dialysis machine for the removal of toxic substances from biological fluids with agents for the decalcification of a dialysis liquid circulation is disclosed. The dialysis machine allows measurement of the degree of calcification of the dialysis liquid through the use of a blood leak detector or by measuring the dialysis machine pump flow or pump voltage. The invention also includes a process for automatically decalcifying the dialysis liquid circulation when a predetermined degree of calcification of the dialysis machine is measured.

14 Claims, 1 Drawing Sheet

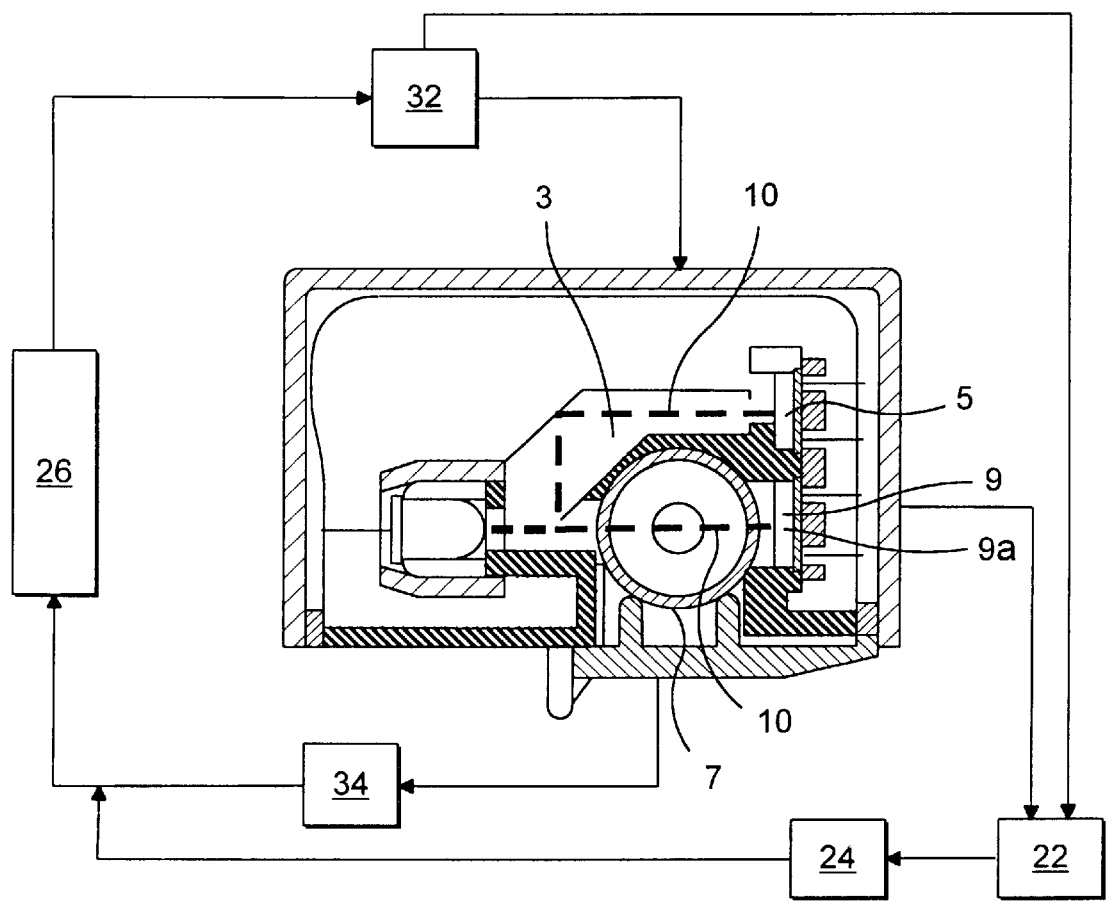
F I G. 1

DIALYSIS MACHINE FOR THE REMOVAL OF TOXIC SUBSTANCES FROM THE BLOOD WITH AGENTS FOR THE DECALCIFICATION OF A DIALYSIS LIQUID CIRCULATION AS WELL AS PROCESS FOR DETERMINING THE DEGREE OF CALCIFICATION OF A DIALYSIS MACHINE

FIELD OF THE INVENTION

The present invention relates to a dialysis machine for the removal of toxic substances from the blood with agents for the decalcification of a dialysis liquid circulation. The invention further relates to processes for determination of the degree of calcification of a dialysis machine.

BACKGROUND OF THE INVENTION

In bicarbonate dialysis for the removal of toxic substances from the blood, the problem arises that bicarbonate and calcium form a poorly soluble precipitate. The components in bicarbonate dialysis are therefore kept separate as sodium bicarbonate in the basic component and as calcium chloride, in the acid component, and then mixed only in the machine itself or shortly before use.

In spite of this measure, seed crystals form in the dialysis machine, which in time leads to extensive deposits of calcium carbonate. For this reason, it becomes necessary to decalcify a dialysis machine from time to time. The usual decalcifying agents are, for example, acetic acid or citric acid.

U.S. Pat. No. 5,326,476 teaches how to introduce a manually operable or time-controlled decalcification cycle.

These decalcification methods prove to be disadvantageous to the extent that the manual selection of a decalcifying program must be made by service personnel, which as a rule turns out to be very time-consuming. Time-controlled decalcification, moreover, has the disadvantage that decalcification is effected even when the degree of calcification would not yet require such decalcification. This leads to unnecessary demands being placed on the decalcification device. Furthermore, the dialysis machine is not available for actual treatments during this period.

OBJECTS AND SUMMARY OF THE INVENTION

The object of the invention is therefore to create a dialysis machine with a decalcifying device which will obviate the above disadvantages.

The invention has the further goal of providing indicating processes that can be advantageously used in determining the degree of calcification of a dialysis machine.

Pursuant to the invention, this object is achieved by a dialysis machine as described and claimed herein.

With the dialysis machine according to the invention, decalcification is automatically initiated only as a function of the state of calcification actually measured. This prevents placing demands on the operating personnel as well as unnecessary use of the decalcifying agents.

Preferred embodiments are the subject of subclaims.

According to one advantageous further development, the degree of calcification of the dialysis machine can be determined through the clouding of the window of a blood leak detector. The fact exploited here is that, with increasing calcification of a dialysis liquid circulation, lime deposits will also form on the window of the blood leak detector of the dialysis machine, which results in the weakening of a light ray passing through such a window.

According to a further advantageous embodiment, the degree of calcification of the dialysis machine can be determined by determining the clouding of the dialysis fluid used; the clouding of the dialysis fluid is associated with an increasing degree of calcification of the dialysis liquid circulation and/or increasing lime deposition. This represents a simple and reliable method for determining the degree of calcification of a dialysis machine, which can be carried out, for example, continuously or discontinuously, i.e., at specified intervals.

It is of particular advantage to use a blood leak detector of a dialysis machine which has a signal output that reacts to clouding of the dialysis liquid and/or clouding of the window of the blood leak detector. This represents an especially simple process in which an available blood leak detector need only be equipped with another signal output.

According to a further advantageous embodiment, the degree of calcification of the dialysis machine can be determined by means of characteristic parameters of a pump, especially a gear pump, which serves to convey the dialysis liquid through the dialysis machine. This determination process can also be carried out in a very simple and reliable way, since certain characteristic parameters of a gear pump are changed in specific ways by increasing calcification.

It is found to be particularly advantageous to determine the degree of calcification on the basis of a change in the dialysis liquid flow discharged by the pump.

It is also possible to determine the degree of calcification on the basis of a change in the pump voltage and/or the pump delivery.

According to a further advantageous development, the dialysis machine has means which, when a predetermined degree of calcification is detected, store this information and do not initiate automatic decalcification until a dialysis is terminated. This ensures that the dialysis operation is in no way hindered.

According to a further design of the invention, provision is made to use the acid component of the bicarbonate dialysis fluid as the decalcifying agent. This provides an especially simple means for the decalcification of a dialysis machine.

According to one process of the invention for determining the degree of calcification of a dialysis machine, the clouding of a window, such as an observation window, of a blood leak detector of a dialysis machine is determined, and the data thus obtained is correlated with a degree of calcification of the dialysis machine. This is shown to be an advantage because the degree of calcification and, hence, the clouding of an observation window of a blood leak detector, is dependent on the degree of calcification of the dialysis liquid circulation.

In further accordance with a process of the invention for determining the degree of calcification of a dialysis machine, the degree of clouding of a dialysis liquid used is determined, and the data thus obtained is correlated with a degree of calcification of a dialysis machine. This makes use of the fact that there is a definite relation between the degree of clouding of the dialysis liquid used and the actual degree of calcification of a dialysis machine.

Of particular advantage in this invention, is to determine the degree of clouding by means of a blood leak detector signal output reacting to clouding. To this end it is only necessary to provide a conventional blood leak detector with a signal output or signal channel which reacts to largely color-unspecified clouding, as may be caused, for example, by the clouding of a window and/or of the dialysis liquid. By arranging a suitable sensor of the blood leak detector inside the dialysis liquid circulation, such clouding is produced by $CaCO_3$ deposits on the sensor itself. However, it is also possible to arrange such a sensor in some other position in relation to the dialysis liquid circulation.

The invention further provides a process in which at least one characteristic parameter of a pump, especially a gear pump, that serves to convey dialysis liquid through the dialysis machine, is determined, and the parameter value thus determined is correlated with a degree of calcification. It has been determined, in fact, that the operating or performance parameters of gear pumps change in some way as a result of calcification.

It has proven particularly advantageous to use as a characteristic parameter the dialysis liquid flow delivered by the gear pump, or the delivery or voltage of the gear pump. These parameters can be easily and reliably measured and can be correlated unequivocally with the actual degree of calcification of the dialysis machine.

DETAILED DESCRIPTION OF THE PREFERRED EMBODIMENTS

Preferred embodiments of the invention are described in greater detail with reference to the appended drawing.

FIG. 1 is a schematic view of the design of a blood leak detector that, in accordance with a preferred embodiment of the invention, can be used to determine the degree of calcification of a dialysis machine.

A blood leak detector has, for example, a bicolor LED 1, which alternately radiates an orange-red and a green light (light ray 10). Approximately 50% of this light is decoupled via a prism 3 and led to the reference receiver 5. This reference receiver 5 forms the input of a reference channel. The reference channel regulates the light intensity of the two colors in such a way that they are in a fixed ratio to one another. The remaining light radiates through a cell 7 and the medium in it (e.g., dialysis liquid). Afterwards this light hits a measuring and cell receiver 9. If there is blood in the dialysis liquid, the green light undergoes a loss of intensity when it radiates through the cell. The thereby changed intensity ratio is evaluated in a measuring channel following the measuring receiver 9.

According to a preferred embodiment of the present invention, a dialysis machine has a blood leak detector equipped with an additional signal output or signal channel which reacts to clouding (clouding receiver 9a or clouding channel). An electronic circuit or its balance is hereby preferably so designed that when no clouding is present the output voltage is 5 volt. With increasing calcification during bicarbonate dialysis this output voltage decreases because of increased clouding. If this voltage drops below a specific threshold value, e.g., 3.5 volts, a decalcification cycle is automatically started. For this, a microprocessor-controlled valve, 24 for example, can be activated in such a way that a suitable decalcifying agent is introduced into the dialysis liquid circulation 26. In particular, it is thereby possible, for example by computer 22 control of the system, to set or generate a flag or trigger signal for the decalcification cycle that initiates the actual decalcification only after the dialysis procedure.

The presence of blood in the dialysis liquid is therefore detected via a measuring channel, as is the onset of clouding of the dialysis liquid via a clouding channel. Signal processing of the measuring channel or the blood leak channel occurs when a photoelectric cell converts the light signals received from the two-color LED to a logarithmic voltage with reference to the light intensity received, so that square-wave amplitude produced by the alternating red-green lighting is proportional to the logarithm of the red-green quotient and that color-unspecific clouding, which attenuate the two colors equally, do not affect the signal. However, if blood is found in the dialysis liquid, the green light undergoes a loss of intensity, as described above, so that the changed ratio can be evaluated by the measuring channel. The clouding channel is so designed that its output voltage continues to decrease with increased clouding.

According to a further preferred form of embodiment, the degree of calcification of a dialysis machine is determined by evaluation of specific parameters of a gear pump 32 used to deliver the dialysis liquid.

Dialysis machines are known to insert such gear pumps for the delivery of dialysis fluid. Because of the increasing calcification in bicarbonate dialysis, the characteristic parameters of this gear pump change. If such calcification occurs, for example, with the use of dialysis machines with constant-voltage operation of the gear pump or feed pump, the calcification is expressed, for example, by an increase of the dialysis liquid flow.

When a certain level of flow is exceeded, for example by 20%, it is then possible to start a decalcification cycle automatically. Here, too, it is possible to generate an alarm signal and to set or generate a flag signal or trigger signal for a decalcification cycle that would initiate the actual decalcification only after the dialysis ends. It is likewise possible to use other pump 32 parameters to determine the degree of calcification, for example the increase or decrease of the delivery and/or the voltage of the pump 32, depending on the pump 32 control used.

Common to the invention embodiments is that they provide agents for starting automatic decalcification when a predetermined degree of calcification of the dialysis machine is detected. As examples, decalcifying agents such as acetic acid, peracetic acid, or citric acid may be used.

According to a preferred form of embodiment, acid components used in bicarbonate dialysis can also be used for the decalcification. This is possible because these components for the most part contain acetate. It is thus possible to largely avoid complete disinfection cycles with other lime-dissolving disinfecting agents.

Substantial advantages here are that neither a supplementary reservoir for the decalcifying agent nor a supplementary device for delivering the decalcifying agent is needed. Moreover, no connection or change in the connection of the dialysis machine need be made prior to the start of the decalcification cycle since the acid component is already connected to the dialysis machine, whether by being supplied from a canister or via a central supply attachment. When the above-mentioned criteria for decalcification are present, for example after recognition of the state where the "dialysis has ended," the dialysis machine can then initiate the decalcification cycle fully automatically.

According to the invention, therefore, the decalcification of a dialysis machine is simplified in such a way that a simple, user-friendly, and reliable regeneration of the dialysis machine is assured. The success of the decalcification itself as well as the safety of the patient is thereby assured.

To further enhance safety, it is possible to provide means 34 which are capable, after the end of the decalcification cycle, to detect remnants of the decalcifying agent used, so as to be able to effectively avoid that decalcifying agent residues remain in the dialysis machine.

What is claimed is:

1. A dialysis machine for the removal of toxic substances from biological fluids having a means for decalcification of the dialysis machine, a means for determining the degree of calcification of the dialysis machine, and a means for automatically initiating decalcification of the dialysis machine as a function of the degree of calcification of the dialysis fluid.

2. The invention of claim 1 further comprising a means of initiating decalcification only when dialysis treatment is not being performed.

3. The invention of claim 1 wherein the means of decalcification comprises the use of the acid component of the bicarbonate dialysis fluid.

4. The invention of claim 1, wherein the means for determining the degree of calcification of the dialysis machine comprises a means for determining the clouding of a window of a blood leak detector.

5. The invention of claim 4 further comprising a signal output which responds to the clouding of the observation window of a blood leak detector.

6. The invention of claim 5 wherein the signal output reacts to largely color unspecified clouding.

7. The invention of claim 1, further comprising a means of storing the information that a predetermined level of calcification has been detected and initiating decalcification only alter the end of a patient's dialysis treatment.

8. The invention of claim 1, wherein the means of decalcification comprises the use of the acid component of the bicarbonate dialysis fluid.

9. The invention of claim 1, wherein a decalcifying agent is selected from the group of acetic acid, peracetic acid and citric acid.

10. The invention of claim 1, further comprising a means of detecting remnants of decalcifying agents following the decalcification procedure.

11. The invention of claim 4 wherein the measured clouding of the window of a blood leak detector is correlated with the degree of calcification of the dialysis machine.

12. A method for automatically decalcifying a dialysis machine comprising the steps of:
    (a) determining the degree of calcification of the dialysis machine; and
    (b) automatically initiating decalcification of the dialysis machine when the degree of calcification reaches a predetermined level.

13. The method of claim 12, wherein step (a) further comprises the steps of:
    (a) determining the degree of clouding of a window of a blood leak detector; and
    (b) correlating the degree of clouding with the degree of calcification of the dialysis machine.

14. The method of claim 12, further comprising the step of initiating the decalcification of the dialysis machine after a dialysis procedure is completed.

* * * * *